(12) United States Patent
Kikutani et al.

(10) Patent No.: US 7,462,461 B2
(45) Date of Patent: Dec. 9, 2008

(54) COMPOSITIONS FOR INHIBITING SEMA7A AND VLA-1 INTERACTION AND THE METHODS OF USING THE SAME

(75) Inventors: Hitoshi Kikutani, Osaka (JP); Atsushi Kumanogoh, Osaka (JP); Kenji Sugiyama, Hyogo (JP)

(73) Assignees: Boehringer Ingelheim International GmbH, Ingelheim (DE); Osaka University, Yamadaoka, Suita-Shi, Osaka (JP)

( * ) Notice: Subject to any disclaimer, the term of this patent is extended or adjusted under 35 U.S.C. 154(b) by 0 days.

(21) Appl. No.: 11/550,184

(22) Filed: Oct. 17, 2006

(65) Prior Publication Data
US 2007/0264263 A1 Nov. 15, 2007

(30) Foreign Application Priority Data
May 12, 2006 (DE) .................. 20 2006 007 590 U

(51) Int. Cl.
*G01N 33/53* (2006.01)
*C07K 14/00* (2006.01)
(52) U.S. Cl. ...................... 435/7.1; 530/350
(58) Field of Classification Search .................. 435/7.1; 530/350
See application file for complete search history.

(56) References Cited

U.S. PATENT DOCUMENTS

| 5,010,175 A | 4/1991 | Rutter et al. |
| 5,266,684 A | 11/1993 | Rutter et al. |
| 5,789,650 A | 8/1998 | Lonberg et al. |
| 5,798,230 A | 8/1998 | Bornkamm et al. |

FOREIGN PATENT DOCUMENTS

| WO | WO 91/19813 | 12/1991 |
| WO | WO 92/02536 | 2/1992 |
| WO | WO 93/03172 | 2/1993 |
| WO | WO 03/080673 | 10/2003 |

OTHER PUBLICATIONS

Kohler et at., 1975, Nature 256: 495-497, "Continuous Cultures of Fused Cells Secreting Antibody of Predefined Specificity".
Boerner et al., 1991, J. Immunol. 147:86-95, "Production of Antigen-specific Human Monoclonal Antibodies from In Vitro-Primed Human Splenocytes".
Persson et al., 1991, Proc. Nat. Acad. Sci. USA 88: 2432-2436, "Generation of diverse high-affinity human monoclonal antibodies by repertoire cloning".
Huang and Stollar, 1991, J. Immunol Methods 141:227-236, "Construction of representative immunoglobulin variable region CDNA libraries from human peripheral blood lymphocytes without in vitro stimulation".

(Continued)

*Primary Examiner*—Karen Cochrane Carlson
(74) *Attorney, Agent, or Firm*—Mary-Ellen M. Devlin; Anthony P. Bottino; Philip I. Datlow

(57) ABSTRACT

Disclosed are compositions and methods of treating a cytokine mediated diseases by inhibiting Sema7A and VLA-1 interaction.

3 Claims, 2 Drawing Sheets

Sema7A stimulates monocytes and macrophages

A  Activation of human monocytes

B  Activation of mouse BMMCs

OTHER PUBLICATIONS

Hanayama R, Tanaka M, Miwa K, Shinohara A, Iwamatsu A, Nagata S (2002) Identification of a factor that links apoptotic cells to phagocytes. Nature 417 182-7.

Kolodkin, A. L., Matthes, D. J., and Goodman, C. S. (1993). The semaphorin genes encode a family of transmembrane and secreted growth cone guidance molecules. Cell 75, 1389-1399.

Pasterkamp, R. J., and Kolodkin, A. L. (2003). Semaphorin junction: making tracks toward neural connectivity. Curr Opin Neurobiol 13, 79-89.

Kikutani, H., and Kumanogoh, A. (2003). Semaphorins in interactions between T cells and antigen-presenting cells. Nat Rev Immunol 3, 159-167.

Xu, X., Ng, S., Wu, Z. L., Nguyen, D., Hamburger, S., Seidel-Dugan, C., Ebens, A. and Luo, Y. (1998). Human semaphorin K1 is glycosylphosphatidylinositol-linked and defines a new subfamily of viral-related semaphorins. J Biol Chem 273, 22428-2234.

Tamagnone, L., Artigiani, S., Chen, H., He, Z., Ming, G. I., Song, H., Chedotal, A., Winberg, M. L., Goodman, C. S., Poo, M. et al. (1999). Plexins are a large family of receptors for transmembrane, secreted, and GPI-enchored semaphorins in vertebrates. Cell 99, 71-80.

Pasterkamp, R. J., Peschon, J. J., Spriggs, M. K., and Kolodkin, A. L. (2003). Semaphorin 7A promotes axon outgrowth through integrins and MAPKs. Nature 424, 398-405.

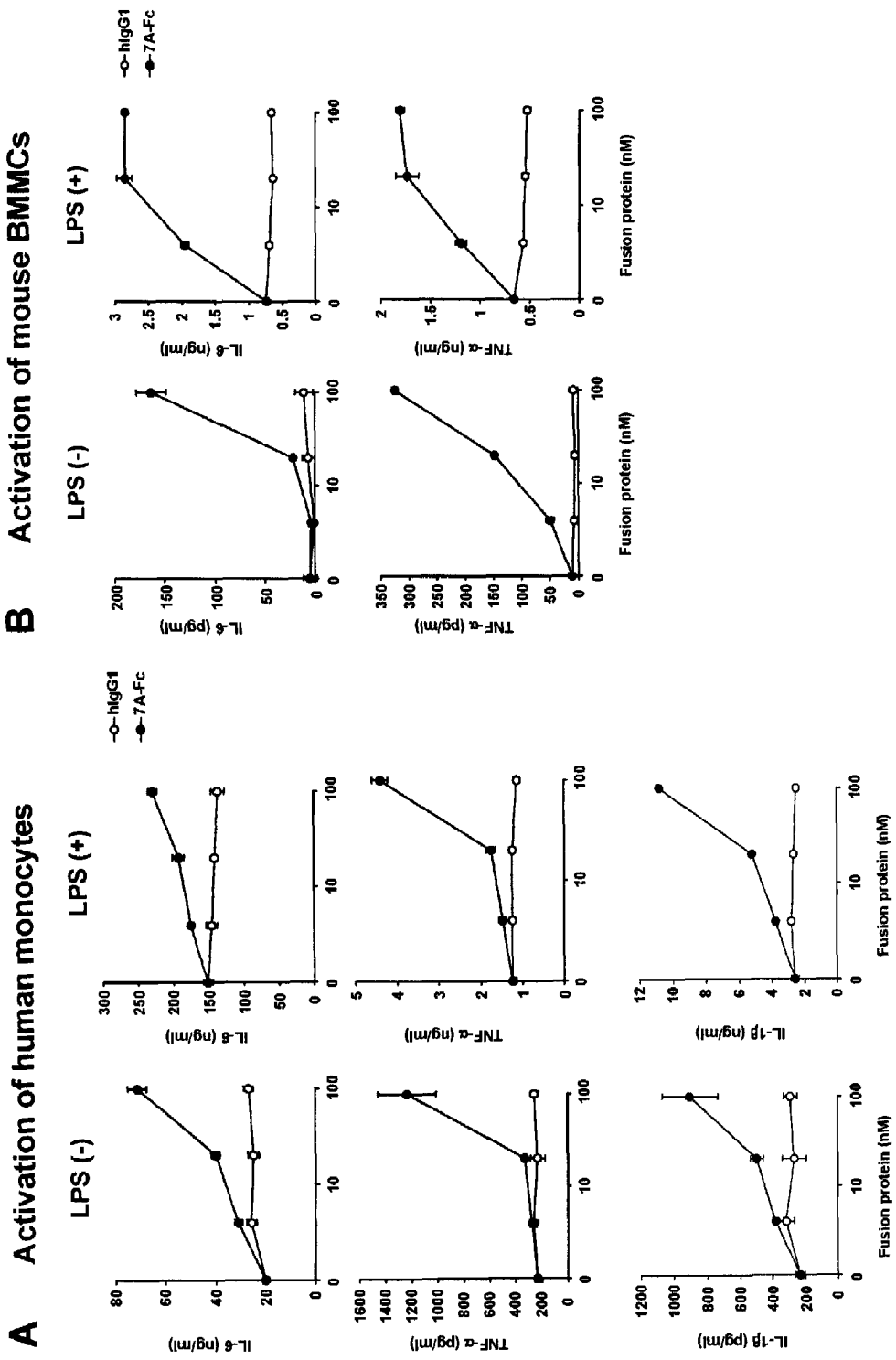
Figure 1. Sema7A stimulates monocytes and macrophages

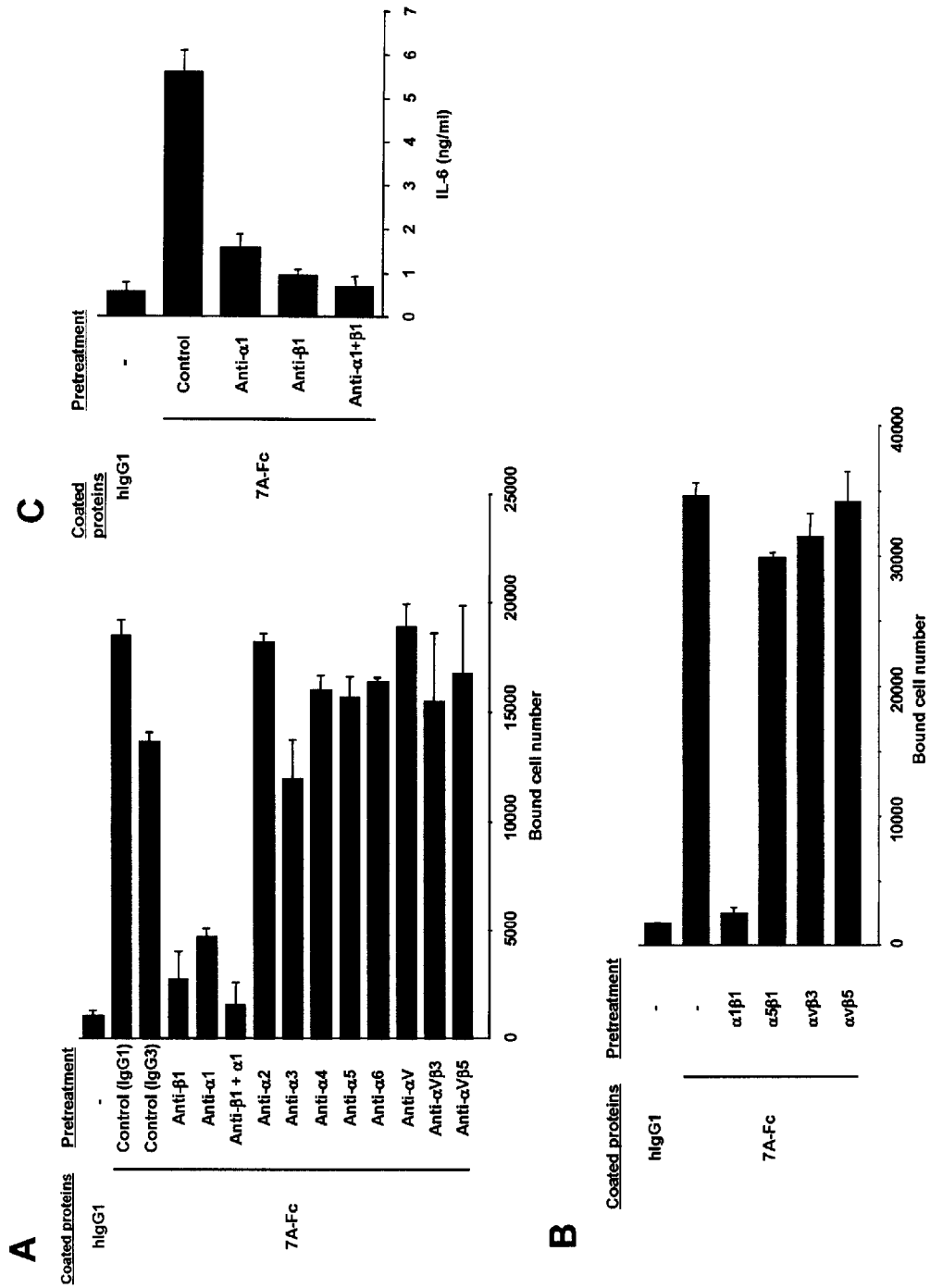
Figure 2. α1β1 integrin is the receptor for Sema7A

COMPOSITIONS FOR INHIBITING SEMA7A AND VLA-1 INTERACTION AND THE METHODS OF USING THE SAME

APPLICATION DATA

This application claims benefit to German Application DE 20 2006 007 590.9 filed May 12, 2006.

BACKGROUND OF THE INVENTION

1. Technical Field

This invention relates to compositions and methods of treating a cytokine mediated disease by inhibiting Sema7A and VLA-1 interaction.

2. Background Information

Semaphorin family consists of a large number of phylogenetically conserved soluble and transmembrane proteins, many of which play diverse roles in axon guidance, organogenesis, angiogenesis, vascularization, oncogenesis and immune responses (1-3). Sema7A, of which expression is observed in both nervous and immune systems, is the only GPI-anchored semaphorin, and it was originally identified in a search for vertebrate homologues of virally-encoded semaphorins. Although Sema7A was shown to bind plexin-C1 (5), it has been suggested recently that Sema7A promotes axon outgrowth through β1-integrin in a plexin-C1-independent manner (6). However, it remains unclear how and to what extent Sema7A is involved in immune responses.

BRIEF SUMMARY OF THE INVENTION

It is therefore an object of the invention to provide a method of treating an inflammatory disease, by administering to a patient a composition which inhibits Sema7A-VLA-1 interaction.

It is yet still another object of the invention to provide a method to identify a compound that controls interaction of Sema7A with VLA-1 activity in a cell, comprising: (1) contacting a cell with a putative regulatory compound, wherein the cell includes a Sema7A protein and a VLA-1 protein; and (2) assessing the ability of the putative regulatory compound to inhibit the interaction of Sema7A with VLA-1.

It is yet still another object of the invention to provide a composition that controls interaction of Sema7A with VLA-1 activity in a cell wherein the composition is therapeutically useful in treating an inflammatory disease.

BRIEF DESCRIPTION OF THE FIGURES

FIG. 1: mouse Sema7A fused with the Fc portion of human IgG1 (Sema7A-Fc) induced production of inflammatory cytokines in not only mouse bone marrow-derived macrophages but also human monocytes.

FIG. 2: the binding of Sema7A to human monocytic cells was inhibited not only by anti-β1 Ab and/or anti-α1 Ab but also by soluble α1β1-integrin. Also shown is the production of IL-6 induced by Sema7A which was blocked by the Abs.

DETAILED DESCRIPTION OF THE INVENTION

In a first generic embodiment, there is provided a method of treating cytokine mediated disease, by administering to a patient a composition which inhibits Sema7A and VLA-1 interaction.

The present inventors have identified that Sema7A, which is expressed on the cell surface of activated T-cells, is crucially involved in activation of human monocytic cells. As shown in FIG. 1, mouse Sema7A fused with the Fc portion of human IgG1 (Sema7A-Fc) induced production of inflammatory cytokines in not only mouse bone marrow-derived macrophages but also human monocytes. Sema7A-Fc also enhanced LPS-induced production of cytokines in these cells. (The amino acid identity between mouse and human Sema7A is 90%.) In addition, the binding of Sema7A to human monocytic cells was inhibited not only by anti-β1 Ab and/or anti-α1 Ab but also by soluble α1β1-integrin (FIG. 2). Furthermore, the production of IL-6 induced by Sema7A was significantly blocked by the Abs (FIG. 2). Collectively, our finding not only indicates a role of Sema7A in the immune system but also identifies the involvement of α1β1-integrin (VLA-1) as a receptor for Sema7A in activation of monocytes. Therefore, the interaction between Sema7A and α1β1-integrin (VLA-1) will be a potential therapeutic target for various inflammatory diseases.

FIG. 1 shows that Sema7A is a potent stimulator for monocytes. (A) and (B) Human monocytes or mouse bone marrow-derived macrophages were cultured on Sema7A-Fc-coated or human IgG1-coated plates with or without LPS (100 ng/ml) for 24 hr. Production of the indicated cytokines in the culture supernatants was measured by ELISA. Results were the means of triplicate determinations.

Method: Human monocytes were isolated from peripheral blood of volunteers by using RosseteSep human monocyte enrichment cocktail (StemCell Technologies). Mouse bone marrow-derived macrophages were obtained from 5-day culture of bone marrow cells in the presence of G-CSF (50 ng/ml; Peprotec). Cells were plated onto flat-bottomed 96-well plates coated with the indicated concentrations of Sema7A-Fc or human IgG1 ($1 \times 10^5$ cells/well in 200 µl of RPMI1640 medium supplemented with 10% FCS) and incubated for 24 hours. The concentrations of cytokines in the culture supernatants were measured by ELISA kits (R&D Systems).

FIG. 2 shows that α1β1integrin/VLA-1 is a functional receptor for Sema7A.

(A) Adhesion of THP-1 cells, a human monocytic cell line, to Sema7A-coated plates was blocked with both anti-β1 and anti-α1 integrin Abs. THP-1 cells were pre-incubated with the indicated antibodies (25 µg/ml) and subjected to adhesion assays. The number of cells attached to Sema7A-coated wells was quantified as previously described (6, 7).

(B) Adhesion of THP-1 cells to immobilized Sema7A was inhibited in the presence of soluble α1β1 integrin proteins. Sema7A-coated wells were pre-treated with the indicated soluble integrin proteins before applying THP-1 cells.

(C) Sema7A-induced cytokine production by human monocytes was inhibited by anti-β1 and anti-α1 integrin Abs. Human monocytes were pretreated with 10 µg/ml of the indicated Abs and then seeded on to Sema7A-coated plates. Production of IL-6 in the culture supernatants were measured by ELISA.

Method: Tissue culture plates (96-well, suspension culture treated, SUMILON) were coated overnight with 100 µl/well of 10 nM fusion protein solutions, followed by blocking with 10 mg/ml BSA in PBS buffer (200 µl/well). Cells were added at $5 \times 10^4$ cells/well in 200 µl of Tyrode buffer (135 mM NaCl, 5.4 mM KCl, 1.0 mM $MgCl_2$, 5 mM NaOH-Hepes(pH7.4), 10 mM Glucose, 10 mg/ml BSA) and allowed to adhere for 1 hour at room temperature. Wells were then washed 3 times in prewarmed PBS buffer. The number of adherent cells was determined by CyQUANT cell proliferation assay kit (Molecular probe). For antibody blocking assays, THP-1 cells were incubated on ice with 25 µg/ml of the indicated anti-integrin antibodies in Tyrode buffer for 30 min. Soluble forms of integrin proteins were used for pretreateatment of Sema7A-Fc-coated wells at 1 μM in Tyrode buffer and plates were incubated for 30 min at room temperature.

One embodiment of the present invention relates to a method to identify a compound that controls interaction of Sema7A with VLA-1 activity in a cell, comprising: (1) contacting a cell with a putative regulatory compound, wherein the cell includes a Sema7A protein and a VLA-1 protein; and (2) assessing the ability of the putative regulatory compound to inhibit the interaction of Sema7A with VLA-1. The assessment step preferably involves studying the adhesion of THP-1 cells to Sema7A or equivalent methods known in the art.

The term "regulate" refers to controlling the activity of a molecule and/or biological function, such as enhancing or diminishing such activity or function.

The term "patient" includes both human and non-human mammals.

The terms "treating" or "treatment" mean the treatment of a disease-state in a patient, and include:
 (i) preventing the disease-state from occurring in a patient, in particular, when such patient is genetically or otherwise predisposed to the disease-state but has not yet been diagnosed as having it;
 (ii) inhibiting or ameliorating the disease-state in a patient, i.e., arresting or slowing its development; or
 (iii) relieving the disease-state in a patient, i.e., causing regression or cure of the disease-state.

Yet another embodiment of the present invention relates to an antibody or antibody binding site which binds Sema7A, VLA-1 or fragments thereof. Embodiments of the present invention further include polyclonal and monoclonal antibodies. Preferred embodiments of the present invention include a monoclonal antibody such an anti-VLA-1 monoclonal antibody. The above antibody or antibody binding site which binds Sema7A or VLA-1 inhibits binding of Sema7A with VLA-1.

Yet another embodiment of the present invention relates to a biotherapeutic comprising Sema7A or VLA-1 protein or fragments thereof, wherein the biotherapeutic is useful for treating an inflammatory disease.

The term "composition" as referred to herein include a putative compound, or a substantially pure protein selected from Sema7A and VLA-1 or fragments thereof, an antibody or antibody binding site which binds Sema7A and VLA-1 or fragments thereof, to an expression vector encoding Sema7A, VLA-1 or fragments thereof, a fusion protein comprising Sema7A, VLA-1 or fragments thereof. In the antibody binding site embodiments, the antibody binding site may be: specifically immunoreactive with a mature protein selected from the group consisting of the Sema7A and VLA-1; raised against a purified or recombinantly produced human or mouse Sema7A or VLA-1; in a monoclonal antibody, Fab, or F(ab)2; immunoreactive with denatured antigen; or in a labeled antibody. In certain embodiments; the antibody binding site is detected in a biological sample by a method of: contacting a binding agent having an affinity for Sema7A or VLA-1 with the biological sample; incubating the binding agent with the biological sample to form a binding agent: Sema7A or VLA-1 protein complex; and detecting the complex. In a preferred embodiment, the biological sample is human, and the binding agent is an antibody.

Putative compounds as referred to herein include, for example, compounds that are products of rational drug design, natural products and compounds having partially defined signal transduction regulatory properties. A putative compound can be a protein-based compound, a carbohydrate-based compound, a lipid-based compound, a nucleic acid-based compound, a natural organic compound, a synthetically derived organic compound, an anti-idiotypic antibody and/or catalytic antibody, or fragments thereof. A putative regulatory compound can be obtained, for example, from libraries of natural or synthetic compounds, in particular from chemical or combinatorial libraries (i.e., libraries of compounds that differ in sequence or size but that have the same building blocks; see for example, U.S. Pat. Nos. 5,010,175 and 5,266,684 of Rutter and Santi, which are incorporated herein by reference in their entirety) or by rational drug design.

In a rational drug design procedure, the three-dimensional structure of a compound, such as a signal transduction molecule can be analyzed by, for example, nuclear magnetic resonance (NMR) or x-ray crystallography. This three-dimensional structure can then be used to predict structures of potential compounds, such as putative regulatory compounds by, for example, computer modelling. The predicted compound structure can then be produced by, for example, chemical synthesis, recombinant DNA technology, or by isolating a mimetope from a natural source (e.g., plants, animals, bacteria and fungi). Potential regulatory compounds can also be identified using SELEX technology as described in, for example, PCT Publication Nos. WO 91/19813; WO 92/02536 and WO 93/03172 (which are incorporated herein by reference in their entirety).

In particular, a naturally-occurring intracellular signal transduction molecule can be modified based on an analysis of its structure and function to form a suitable regulatory compound. For example, a compound capable of regulating the Sema7A or VLA-1 can comprise a compound having similar structure to the amino acid residues in their respective binding domains. Such a compound can comprise a peptide, a polypeptide or a small organic molecule.

Putative regulatory compounds can also include molecules designed to interfere with Sema7A or VLA-1. For example, mutants of VLA-1 can be created that interfere with the coupling of the protein with Sema7A. Putative regulatory compounds can include agonists and antagonists of Sema7A or VLA-1. Such agonists and antagonists can be selected based on the structure of a naturally-occurring ligand to these proteins.

The technology for producing monoclonal antibodies is well known. In general, an immortal cell line (typically myeloma cells) is fused to lymphocytes (typically splenocytes) from a mammal immunized with whole cells expressing a given antigen, e.g., Sema7A or VLA-1, and the culture supernatants of the resulting hybridoma cells are screened for antibodies against the antigen. See, generally, Kohler et at., 1975, Nature 265: 295-497, "Continuous Cultures of Fused Cells Secreting Antibody of Predefined Specificity".

Immunization may be accomplished using standard procedures. The unit dose and immunization regimen depend on the species of mammal immunized, its immune status, the body weight of the mammal, etc. Typically, the immunized mammals are bled and the serum from each blood sample is assayed for particular antibodies using appropriate screening assays. For example, anti-integrin antibodies may be identified by immunoprecipitation of 125I-labeled cell lysates from integrin-expressing cells. Antibodies, including for example, anti-VLA-1 antibodies, may also be identified by flow cytometry, e.g., by measuring fluorescent staining of antibody-expressing cells incubated with an antibody believed to recognize VLA-1 molecules. The lymphocytes used in the production of hybridoma cells typically are isolated from immunized mammals whose sera have already tested positive for the presence of anti-VLA-1 antibodies using such screening assays.

Typically, the immortal cell line (e.g., a myeloma cell line) is derived from the same mammalian species as the lymphocytes. Preferred immortal cell lines are mouse myeloma cell lines that are sensitive to culture medium containing hypoxanthine, aminopterin and thymidine ("HAT medium"). Typically, HAT-sensitive mouse myeloma cells are fused to mouse splenocytes using 1500 molecular weight polyethylene glycol ("PEG 1500"). Hybridoma cells resulting from the fusion are then selected using HAT medium, which kills unfused and unproductively fused myeloma cells (unfused splenocytes die after several days because they are not transformed). Hybridomas producing a desired antibody are detected by screening the hybridoma culture supernatants. For example, hybridomas prepared to produce anti-VLA-1 antibodies may be screened by testing the hybridoma culture supernatant for secreted antibodies having the ability to bind to a recombinant VLA-1 expressing cell line.

To produce antibody homologs which are within the scope of the invention, including for example, anti-VLA-1 antibody homologs, that are intact immunoglobulins, hybridoma cells that tested positive in such screening assays were cultured in a nutrient medium under conditions and for a time sufficient to allow the hybridoma cells to secrete the monoclonal antibodies into the culture medium. Tissue culture techniques and culture media suitable for hybridoma cells are well known. The conditioned hybridoma culture supernatant may be collected and the anti-VLA-1 antibodies optionally further purified by well-known methods.

Alternatively, the desired antibody may be produced by injecting the hybridoma cells into the peritoneal cavity of an unimmunized mouse. The hybridoma cells proliferate in the peritoneal cavity, secreting the antibody which accumulates as ascites fluid. The antibody may be harvested by withdrawing the ascites fluid from the peritoneal cavity with a syringe.

Fully human monoclonal antibody homologs against, for example Sema7A or VLA-1, are another preferred binding agent which may block antigens in the method of the invention. In their intact form these may be prepared using in vitro-primed human splenocytes, as described by Boerner et al., 1991, J. Immunol. 147:86-95, "Production of Antigen-specific Human Monoclonal Antibodies from In Vitro-Primed Human Splenocytes".

Alternatively, they may be prepared by repertoire cloning as described by Persson et al., 1991, Proc. Nat. Acad. Sci. USA 88: 2432-2436, "Generation of diverse high-affinity human monoclonal antibodies by repertoire cloning" and Huang and Stollar, 1991, J. Immunol. Methods 141: 227-236, "Construction of representative immunoglobulin variable region CDNA libraries from human peripheral blood lymphocytes without in vitro stimulation". U.S. Pat. No. 5,798,230 (Aug. 25, 1998, "Process for the preparation of human monoclonal antibodies and their use") describes preparation of human monoclonal antibodies from human B cells. According to this process, human antibody-producing B cells are immortalized by infection with an Epstein-Barr virus, or a derivative thereof, that expresses Epstein-Barr virus nuclear antigen 2 (EBNA2). EBNA2 function, which is required for immortalization, is subsequently shut off, which results in an increase in antibody production.

In yet another method for producing fully human antibodies, U.S. Pat. No. 5,789,650 (Aug. 4, 1998, "Transgenic non-human animals for producing heterologous antibodies") describes transgenic non-human animals capable of producing heterologous antibodies and transgenic non-human animals having inactivated endogenous immunoglobulin genes. Endogenous immunoglobulin genes are suppressed by antisense polynucleotides and/or by antiserum directed against endogenous immunoglobulins. Heterologous antibodies are encoded by immunoglobulin genes not normally found in the genome of that species of non-human animal. One or more transgenes containing sequences of unrearranged heterologous human immunoglobulin heavy chains are introduced into a non-human animal thereby forming a transgenic animal capable of functionally rearranging transgenic immunoglobulin sequences and producing a repertoire of antibodies of various isotypes encoded by human immunoglobulin genes. Such heterologous human antibodies are produced in B-cells which are thereafter immortalized, e.g., by fusing with an immortalizing cell line such as a myeloma or by manipulating such B-cells by other techniques to perpetuate a cell line capable of producing a monoclonal heterologous, fully human antibody homolog.

The conditions under which the cell of the present invention is contacted with a putative regulatory compound, such as by mixing, are conditions in which the cell can exhibit Sema7A or VLA-1 activity if essentially no other regulatory compounds are present that would interfere with such activity. Achieving such conditions is within the skill in the art, and includes an effective medium in which the cell can be cultured such that the cell can exhibit Sema7A or VLA-1 activity. For example, for a mammalian cell, effective media are typically aqueous media comprising RPMI 1640 medium containing 10% fetal calf serum.

Cells of the present invention can be cultured in a variety of containers including, but not limited to, tissue culture flasks, test tubes, microtiter dishes, and petri plates. Culturing is carried out at a temperature, pH and carbon dioxide content appropriate for the cell. Such culturing conditions are also within the skill in the art. For example, for Ramos cells, culturing can be carried out at 37.degree. C., in a 5% $CO_2$ environment.

Acceptable protocols to contact a cell with a putative regulatory compound in an effective manner include the number of cells per container contacted, the concentration of putative regulatory compound(s) administered to a cell, the incubation time of the putative regulatory compound with the cell, the concentration of ligand and/or intracellular initiator molecules administered to a cell, and the incubation time of the ligand and/or intracellular initiator molecule with the cell. Determination of such protocols can be accomplished by those skilled in the art based on variables such as the size of the container, the volume of liquid in the container, the type of cell being tested and the chemical composition of the putative regulatory compound (i.e., size, charge etc.) being tested.

In one embodiment of the method of the present invention, a suitable number of cells are added to a 96-well tissue culture dish in culture medium. A preferred number of cells includes a number of cells that enables one to detect a change in VLA-1 or Sema7A activity using a detection method of the present invention (described in detail below). A more preferred number of cells includes between about 1 and 1.times. 10.sup.6 cells per well of a 96-well tissue culture dish. Following addition of the cells to the tissue culture dish, the cells can be preincubated at 37.degree. C., 5% C.sub.2O for between about 0 to about 24 hours.

A suitable amount of putative regulatory compound(s) suspended in culture medium is added to the cells that is sufficient to regulate the activity of a Sema7A or VLA-1 protein in a cell such that the regulation is detectable using a detection method of the present invention. A preferred amount of putative regulatory compound(s) comprises between about 1 nM to about 10 mM of putative regulatory compound(s) per well of a 96-well plate. The cells are allowed to incubate for a suitable length of time to allow the putative regulatory compound to enter a cell and interact with Sema7A or VLA-1 protein. A preferred incubation time is between about 1 minute to about 48 hours.

In another embodiment of the method of the present invention, cells suitable for use in the present invention are stimulated with a stimulatory molecules capable of binding to Sema7A or VLA-1 protein of the present invention to initiate a signal transduction pathway and create a cellular response. Preferably, cells are stimulated with a stimulatory molecule following contact of a putative regulatory compound with a cell. Suitable stimulatory molecules can include, for example, antibodies that bind specifically to Sema7A or VLA-1 protein. A suitable amount of stimulatory molecule to add to a cell depends upon factors such as the type of ligand used (e.g., monomeric or multimeric; permeability, etc.) and the abundance of Sema7A or VLA-1 protein. Preferably, between about 1.0 nM and about 1 mM of ligand is added to a cell.

The method of the present invention include determining if a composition is capable of regulating Sema7A or VLA-1 protein activation. Such methods include assays described in detail in the methods section. The method of the present invention can further include the step of performing a toxicity test to determine the toxicity of the composition.

Another aspect of the present invention includes a kit to identify compositions capable of regulating Sema7A or VLA-1 protein activity in a cell. Such a kit includes: (1) a cell comprising Sema7A or VLA-1 protein; and (2) a means for detecting regulation of either the Sema7A or VLA-1 protein. Such a means for detecting the regulation of Sema7A or VLA-1 protein include methods and reagents known to those of skill in the art, for example, VLA-1 protein activity can be detected using, for example, activation assays described herein-below. Means for detecting the regulation of Sema7A or VLA-1 protein also include methods and reagents known to those of skill in the art. Suitable cells for use with a kit of the present invention include cells described in detail herein. A preferred cell for use with a kit includes a human cell.

METHODS OF THERAPEUTIC USE

As described above, the present inventors have found that Sema7A has a role in the immune system and have also identified the involvement of $\alpha1\beta1$-integrin (VLA-1) as a receptor for Sema7A in activation of monocytes. Therefore, the interaction between Sema7A and $\alpha1\beta1$-integrin (VLA-1) will be a potential therapeutic target for various diseases mediated by cytokines such as inflammatory diseases.

The invention therefore provides a method of treating a cytokine mediated disease, by administering to a patient a composition which inhibits Sema7A and VLA-1 interaction.

A composition which would block the interaction of Sema7A with VLA-1 would block inflammatory cytokine production from cells. The inhibition of cytokine production is an attractive means for preventing and treating a variety of cytokine mediated diseases or conditions associated with excess cytokine production, e.g., diseases and pathological conditions involving inflammation, autoimmune responses or bone resorption. Thus, the compositions are useful for the treatment of diseases and conditions including the following: osteoarthritis, atherosclerosis, contact dermatitis, bone resorption diseases including osteoporosis, reperfusion injury, asthma, multiple sclerosis, Guillain-Barre syndrome, Crohn's disease, ulcerative colitis, psoriasis, graft versus host disease, systemic lupus erythematosus and insulin-dependent diabetes mellitus, rheumatoid arthritis, toxic shock syndrome, Alzheimer's disease, diabetes, inflammatory bowel diseases, acute and chronic pain as well as symptoms of inflammation and cardiovascular disease, stroke, myocardial infarction, alone or following thrombolytic therapy, thermal injury, adult respiratory distress syndrome (ARDS), multiple organ injury secondary to trauma, acute glomerulonephritis, dermatoses with acute inflammatory components, acute purulent meningitis or other central nervous system disorders, syndromes associated with hemodialysis, leukopheresis, granulocyte transfusion associated syndromes, and necrotizing entrerocolitis, complications including restenosis following percutaneous transluminal coronary angioplasty, traumatic arthritis, sepsis, chronic obstructive pulmonary disease and congestive heart failure. Said composition may also be useful for anticoagulant or fibrinolytic therapy (and the diseases or conditions related to such therapy).

Anti-cytokine activity can be demonstrated by using methods known in the art. See for example Branger et al., (2002) *J Immunol.* 168: 4070-4077, and the 46 references cited therein, each incorporated herein by reference in their entirety.

A composition according to the invention will also be useful for treating oncological diseases. These diseases include but are not limited to solid tumors, such as cancers of the breast, respiratory tract, brain, reproductive organs, digestive tract, urinary tract, eye, liver, skin, head and neck, thyroid, parathyroid and their distant metastases. Those disorders also include lymphomas, sarcomas, and leukemias.

Examples of breast cancer include, but are not limited to invasive ductal carcinomas invasive lobular carcinoma, ductal carcinoma in situ, and lobular carcinoma in situ.

Examples of cancers of the respiratory tract include, but are not limited to small-cell and non-small-cell lung carcinoma, as well as bronchial adenoma and pleuropulmonary blastoma and mesothelioma.

Examples of brain cancers include, but are not limited to brain stem, optic and hypophtalmic glioma, cerebella and cerebral astrocytoma, medulloblastoma, ependymoma, as well as pituitary, neuroectodermal and pineal tumor.

Examples of peripheral nervous system tumors include, but are not limited to neuroblastoma, ganglioneuroblastoma, and peripheral nerve sheath tumors.

Examples of tumors of the endocrine and exocrine system include, but are not limited to thyroid carcinoma, adrenocortical carcinoma, pheochromocytoma, and carcinoid tumors.

Tumors of the male reproductive organs include, but are not limited to prostate and testicular cancer.

Tumors of the female reproductive organs include, but are not limited to endometrial, cervical, ovarian, vaginal, and vulvar cancer, as well as sarcoma of the uterus.

Tumors of the digestive tract include, but are not limited to anal, colon, colorectal, esophageal, gallblader, gastric, pancreatic, rectal, small-intestine, and salivary gland cancers.

Tumors of the urinary tract include, but are not limited to bladder, penile, kidney, renal pelvis, ureter, and urethral cancers.

Eye cancers include, but are not limited to intraocular melanoma and retinoblastoma.

Examples of liver cancers include, but are not limited to hepatocellular carcinoma (liver cell carcinomas with or without fibrolamellar variant), hepatoblastoma, cholangiocarcinoma (intrahepatic bile duct carcinoma), and mixed hepatocellular cholangiocarcinoma Skin cancers include, but are not limited to squamous cell carcinoma, Kaposi's sarcoma, malignant melanoma, Merkel cell skin cancer, and non-melanoma skin cancer.

Head-and-neck cancers include, but are not limited to laryngeal/hypopharyngeal/nasopharyngeal/oropharyngeal cancer, and lip and oral cavity cancer.

Lymphomas include, but are not limited to AIDS-related lymphoma, non-Hodgkin's lymphoma, Hodgkins lymphoma, cutaneous T-cell lymphoma, and lymphoma of the central nervous system.

Sarcomas include, but are not limited to sarcoma of the soft tissue, osteosarcoma, Ewings sarcoma, malignant fibrous histiocytoma, lymphosarcoma, angiosarcoma, and rhabdomyosarcoma. Leukemias include, but are not limited to acute myeloid leukemia, acute lymphoblastic leukemia, chronic lymphocytic leukemia, chronic myelogenous leukemia, and hairy cell leukemia.

Plasma cell dyscrasias include, but are not limited to multiple myeloma, and Waldenstrom's macroglobulinemia.

These disorders have been well characterized in man, but also exist with a similar etiology in other mammals, and can be treated by pharmaceutical compositions of the present invention.

For therapeutic use, the compositions may be administered in any conventional dosage form in any conventional manner. Routes of administration include, but are not limited to, intravenously, intramuscularly, subcutaneously, intrasynovially, by infusion, sublingually, transdermally, orally, topically or by inhalation. The preferred modes of administration are oral and intravenous.

The compositions may be administered alone or in combination with adjuvants that enhance stability of the inhibitors, facilitate administration of pharmaceutic compositions containing them in certain embodiments, provide increased dissolution or dispersion, increase inhibitory activity, provide adjunct therapy, and the like, including other active ingredients. Advantageously, such combination therapies utilize lower dosages of the conventional therapeutics, thus avoiding possible toxicity and adverse side effects incurred when those agents are used as monotherapies. The above described compositions may be physically combined with the conventional therapeutics or other adjuvants into a single pharmaceutical composition. Advantageously, the compositions may then be administered together in a single dosage form. In some embodiments, the pharmaceutical compositions comprising such combinations of compositions contain at least about 5%, but more preferably at least about 20%, of a composition (w/w) or a combination thereof. The optimum percentage (w/w) of a composition of the invention may vary and is within the purview of those skilled in the art. Alternatively, the compositions may be administered separately (either serially or in parallel). Separate dosing allows for greater flexibility in the dosing regime.

As mentioned above, dosage forms of the compositions described herein include pharmaceutically acceptable carriers and adjuvants known to those of ordinary skill in the art. These carriers and adjuvants include, for example, ion exchangers, alumina, aluminum stearate, lecithin, serum proteins, buffer substances, water, salts or electrolytes and cellulose-based substances. Preferred dosage forms include, tablet, capsule, caplet, liquid, solution, suspension, emulsion, lozenges, syrup, reconstitutable powder, granule, suppository and transdermal patch. Methods for preparing such dosage forms are known (see, for example, H. C. Ansel and N. G. Popovish, *Pharmaceutical Dosage Forms and Drug Delivery Systems*, 5th ed., Lea and Febiger (1990)). Dosage levels and requirements are well-recognized in the art and may be selected by those of ordinary skill in the art from available methods and techniques suitable for a particular patient. In some embodiments, dosage levels range from about 1-1000 mg/dose for a 70 kg patient. Although one dose per day may be sufficient, up to 5 doses per day may be given. For oral doses, up to 2000 mg/day may be required. As the skilled artisan will appreciate, lower or higher doses may be required depending on particular factors. For instance, specific dosage and treatment regimens will depend on factors such as the patient's general health profile, the severity and course of the patient's disorder or disposition thereto, and the judgment of the treating physician.

All references cited herein, both literature and patent, are hereby incorporated by reference in their entirety.

REFERENCES

1) Kolodkin, A. L., Matthes, D. J., and Goodman, C. S. (1993). The semaphorin genes encode a family of transmembrane and secreted growth cone guidance molecules. Cell 75, 1389-1399.
2) Pasterkamp, R. J., and Kolodkin, A. L. (2003). Semaphorin junction: making tracks toward neural connectivity. Curr Opin Neurobiol 13, 79-89.
3) Kikutani, H., and Kumanogoh, A. (2003). Semaphorins in interactions between T cells and antigen-presenting cells. Nat Rev Immunol 3, 159-167.
4) Xu, X., Ng, S., Wu, Z. L., Nguyen, D., Homburger, S., Seidel-Dugan, C., Ebens, A. and Luo, Y. (1998). Human semaphorin K1 is glycosylphosphatidylinositol-linked and defines a new subfamily of viral-related semaphorins. J Biol Chem 273, 22428-22434.
5) Tamagnone, L., Artigiani, S., Chen, H., He, Z., Ming, G. I., Song, H., Chedotal, A., Winberg, M. L., Goodman, C. S., Poo, M. et al. (1999). Plexins are a large family of receptors for transmembrane, secreted, and GPI-anchored semaphorins in vertebrates. Cell 99, 71-80.
6) Pasterkamp, R. J., Peschon, J. J., Spriggs, M. K., and Kolodkin, A. L. (2003). Semaphorin 7A promotes axon outgrowth through integrins and MAPKs. Nature 424, 398-405.
7) Hanayama R, Tanaka M, Miwa K, Shinohara A, Iwamatsu A, Nagata S (2002) Identification of a factor that links apoptotic cells to phagocytes. Nature 417 182-7.

The invention claimed is:

1. A method to identify a compound that inhibits interaction of Sema7A with VLA-1, comprising:
   (1) contacting a cell with a putative regulatory compound, wherein the cell includes a Sema7A protein and a VLA-1 protein; and
   (2) assessing the ability of the putative regulatory compound to inhibit the interaction of Sema7A with VLA-1.

2. A method to identify a compound that inhibits interaction of Sema7A with VLA-1, comprising:
   (1) contacting a cell with a putative regulatory compound and VLA-1, wherein the cell includes a Sema7A protein; and
   (2) assessing the ability of the putative regulatory compound to inhibit the interaction of Sema7A with VLA-1.

3. A method to identify a compound that inhibits interaction of Sema7A with VLA-1, comprising:
   (1) contacting a cell with a putative regulatory compound and Sema7A, wherein the cell includes a VLA-1 protein; and
   (2) assessing the ability of the putative regulatory compound to inhibit the interaction of Sema7A with VLA-1.

* * * * *